(12) United States Patent
Bouvier et al.

(10) Patent No.: US 9,919,289 B2
(45) Date of Patent: Mar. 20, 2018

(54) ZEOLITE-BASED ADSORBENTS BASED ON LSX ZEOLITE OF CONTROLLED OUTER SURFACE AREA, PROCESS FOR PREPARING THEM AND USES THEREOF

(71) Applicants: IFP ENERGIES NOUVELLES, Rueil-Malmaison (FR); ARKEMA FRANCE, Colombes (FR)

(72) Inventors: Ludivine Bouvier, Orthez (FR); Cécile Lutz, Gan (FR); Catherine Laroche, Charly (FR); Julien Grandjean, Lyons (FR); Arnaud Baudot, Vernaison (FR)

(73) Assignees: IFP Energies Nouvelles, Rueil-Malmaison (FR); Arkema France, Colombes (FR)

( * ) Notice: Subject to any disclaimer, the term of this patent is extended or adjusted under 35 U.S.C. 154(b) by 0 days.

(21) Appl. No.: 15/526,130

(22) PCT Filed: Nov. 13, 2015

(86) PCT No.: PCT/EP2015/076532
§ 371 (c)(1),
(2) Date: May 11, 2017

(87) PCT Pub. No.: WO2016/075281
PCT Pub. Date: May 19, 2016

(65) Prior Publication Data
US 2017/0304800 A1    Oct. 26, 2017

(30) Foreign Application Priority Data

Nov. 13, 2014  (FR) ...................... 14 60953

(51) Int. Cl.
| | | |
|---|---|---|
| *B01J 20/18* | (2006.01) | |
| *C07C 7/13* | (2006.01) | |
| *B01J 20/28* | (2006.01) | |
| *B01J 20/30* | (2006.01) | |
| *B01D 15/18* | (2006.01) | |

(52) U.S. Cl.
CPC .......... *B01J 20/186* (2013.01); *B01D 15/185* (2013.01); *B01D 15/1807* (2013.01); *B01D 15/1828* (2013.01); *B01J 20/2803* (2013.01); *B01J 20/28059* (2013.01); *B01J 20/28061* (2013.01); *B01J 20/28071* (2013.01); *B01J 20/28092* (2013.01); *B01J 20/3028* (2013.01); *B01J 20/3042* (2013.01); *B01J 20/3071* (2013.01); *B01J 20/3085* (2013.01); *C07C 7/13* (2013.01)

(58) Field of Classification Search
CPC .......... B01D 15/1807; B01D 15/1828; B01D 15/185; B01D 53/08; B01D 2253/108; B01D 2253/306; B01D 2253/308; B01D 2253/31; B01D 2253/311; B01D 2255/2022; B01D 2255/2042; B01D 2256/24; B01D 2257/7027; B01D 2259/40086; B01D 2259/4068; B01D 53/02; B01D 2259/4009; B01J 20/183; B01J 20/186; B01J 20/28004; B01J 20/2803; B01J 20/28057; B01J 20/28059; B01J 20/28061; B01J 20/28071; B01J 20/28092; B01J 20/3007; B01J 20/3028; B01J 20/3042; B01J 20/3071; B01J 20/3078; B01J 20/3085; C07C 7/13
See application file for complete search history.

(56) References Cited

U.S. PATENT DOCUMENTS

| | | |
|---|---|---|
| 2,985,589 A | 5/1961 | Broughton et al. |
| 3,558,730 A | 1/1971 | Neuzil et al. |
| 3,558,732 A | 1/1971 | Neuzil et al. |
| 3,626,020 A | 12/1971 | Neuzil |
| 3,663,638 A | 5/1972 | Neuzil |
| 3,878,127 A | 4/1975 | Rosback |
| 3,960,774 A | 6/1976 | Rosback |
| 4,402,832 A | 9/1983 | Gerhold |
| 4,498,991 A | 2/1985 | Oroskar |
| 5,284,992 A | 2/1994 | Hotier et al. |
| 5,629,467 A | 5/1997 | Hotier et al. |
| 6,410,815 B1 | 6/2002 | Plee et al. |
| 6,884,918 B1 | 4/2005 | Plee et al. |

(Continued)

FOREIGN PATENT DOCUMENTS

| | | |
|---|---|---|
| CN | 1267185 C | 8/2006 |
| FR | 2925366 A1 | 6/2009 |
| FR | 3010328 A1 | 3/2015 |
| FR | 3010402 A1 | 3/2015 |
| JP | 11246216 * | 9/1999 |
| WO | 2007043731 A1 | 4/2007 |
| WO | 2013106816 A1 | 7/2013 |
| WO | 2015032923 A1 | 3/2015 |

OTHER PUBLICATIONS

English Translation of JP11246216, pp. 1-16 (Year: 1999).*

(Continued)

*Primary Examiner* — Pancham Bakshi
*Assistant Examiner* — Mark R Luderer
(74) *Attorney, Agent, or Firm* — RatnerPrestia

(57) ABSTRACT

The present invention relates to a zeolite-based adsorbent comprising at least one zeolite of FAU structure of LSX type and comprising barium and/or potassium, in which the outer surface area of said zeolite-based adsorbent, measured by nitrogen adsorption, is between 20 $m^2 \cdot g^{-1}$ and 100 $m^2 \cdot g^{-1}$, limits inclusive. The present invention also relates to the use of such a zeolite-based adsorbent as an adsorption agent, and also to the process for separating para-xylene from aromatic isomer fractions containing 8 carbon atoms.

22 Claims, 2 Drawing Sheets

(56) References Cited

U.S. PATENT DOCUMENTS

| | | | |
|---|---|---|---|
| 7,785,563 B2 | 8/2010 | Ryoo et al. | |
| 8,283,274 B2 | 10/2012 | Cheng | |
| 2009/0326308 A1 | 12/2009 | Kulprathipanja et al. | |
| 2011/0184165 A1* | 7/2011 | Bouvier | B01J 20/18 536/127 |
| 2016/0207025 A1 | 7/2016 | LaRoche et al. | |

OTHER PUBLICATIONS

International Search Report and Written Opinion for International Application No. PCT/EP2015/076532, dated Jan. 25, 2016—11 Pages.

Ruthven, D., "Principles of Adsorption and Adsorption Processes", John Wiley & Sons, 1984, pp. 243, 248-250, 326, 407, and Chapters 8 and 9—453 Pages.

Verboekend te al., "Hierarchical Y and USY Zeolites Designed by Post-Synthetic Strategies", Adv. Funct. Mater., vol. 22, 2012, pp. 916-928.

* cited by examiner

ZEOLITE-BASED ADSORBENTS BASED ON LSX ZEOLITE OF CONTROLLED OUTER SURFACE AREA, PROCESS FOR PREPARING THEM AND USES THEREOF

CROSS-REFERENCE TO RELATED APPLICATIONS

This application is a U.S. National Phase Application of PCT International Application No. PCT/EP2015/076532, filed Nov. 13, 2015 and published May 19, 2016 as WO 2016/075281, which claims priority from French Application No. 1460953 filed Nov. 13, 2014; each of the aforementioned applications is incorporated herein by reference in its entirety for all purposes.

FIELD OF THE INVENTION

The invention relates to zeolite-based adsorbents in the form of agglomerates comprising zeolite of faujasite (FAU) structure of LSX type for their uses in applications in which mass transfer is an important parameter, said adsorbents having a controlled outer surface area, measured by nitrogen adsorption, of between 20 $m^2 \cdot g^{-1}$ and 100 $m^2 \cdot g^{-1}$.

The present invention also relates to a process for preparing said zeolite-based adsorbents, and also to the uses thereof, especially for separating gaseous or liquid mixtures of isomers, more particularly of xylenes and especially for producing very pure para-xylene from an aromatic hydrocarbon feedstock containing isomers containing 8 carbon atoms.

BACKGROUND OF THE INVENTION

The use of zeolite-based adsorbents comprising at least faujasite (FAU) zeolites of X or Y type and comprising, besides sodium cations, barium, potassium or strontium ions, alone or as mixtures, for selectively adsorbing para-xylene in a mixture of aromatic hydrocarbons, is well known from the prior art.

U.S. Pat. No. 3,558,730, U.S. Pat. No. 3,558,732, U.S. Pat. No. 3,626,020 and U.S. Pat. No. 3,663,638 show that zeolite-based adsorbents comprising aluminosilicates based on sodium and barium (U.S. Pat. No. 3,960,774) or based on sodium, barium and potassium, are efficient for separating para-xylene present in C8 aromatic fractions (fractions comprising aromatic hydrocarbons containing 8 carbon atoms).

The adsorbents described in U.S. Pat. No. 3,878,127 are used as adsorption agents in liquid-phase processes, preferably of simulated counter-current type, similar to those described in U.S. Pat. No. 2,985,589 and which apply, inter alia, to C8 aromatic fractions.

Document U.S. Pat. No. 6,884,918 recommends a faujasite X with an Si/Al atomic ratio of between 1.15 and 1.5 exchanged with barium or with barium and potassium. Document U.S. Pat. No. 6,410,815 teaches that zeolite-based adsorbents as described in the prior art, but for which the faujasite has a low content of silica and has an Si/Al atomic ratio close to 1 (which will be referred to as LSX, the abbreviation for low-silica X), are advantageously used for separating para-xylene, especially when feedstocks rich in ethylbenzene need to be treated, due to the better selectivity of para-xylene towards this isomer relative to adsorbents based on zeolite X with an Si/Al atomic ratio of between 1.15 and 1.5.

In the patents listed above, the zeolite-based adsorbents are in the form of crystals in powder form or in the form of agglomerates predominantly consisting of zeolite powder and up to 20% by weight of inert binder.

The synthesis of FAU zeolites is usually performed by nucleation and crystallization of silicoaluminate gels. This synthesis leads to crystals (generally in powder form) whose use at the industrial scale is particularly difficult (substantial losses of feedstocks during the manipulations). Agglomerated forms of these crystals are then preferred, in the form of grains, strands and other agglomerates, these said forms possibly being obtained by extrusion, pelleting, atomization and other agglomeration techniques known to those skilled in the art. These agglomerates do not have the drawbacks inherent in pulverulent materials.

Agglomerates, whether they exist in the form of platelets, beads, extrudates or the like, generally consist of zeolite crystals, which constitute the active element (in the sense of adsorption) and an agglomeration binder. This agglomeration binder is intended to ensure the cohesion of the crystals to each other in the agglomerated structure, but must also give said agglomerates sufficient mechanical strength so as to prevent, or at the very least to minimize, the risks of fractures, splitting or breaks that may arise during their industrial uses during which the agglomerates are subjected to numerous constraints, such as vibrations, high and/or frequent pressure variations, movements and the like.

The preparation of these agglomerates is performed, for example, by pasting zeolite crystals in powder form with a clay paste, in proportions of the order of 80% to 90% by weight of zeolite powder for 20% to 10% by weight of binder, followed by forming into beads, platelets or extrudates, and heat treatment at high temperature for baking of the clay and reactivation of the zeolite, the cation exchange (s), for instance the exchange with barium and optionally with potassium, possibly being performed before and/or after the agglomeration of the pulverulent zeolite with the binder.

Zeolite-based agglomerates are obtained, the particle size of which is a few millimeters, or even of the order of a millimeter, and which, if the choice of the agglomeration binder and the granulation are made according to the rule book, have a satisfactory set of properties, in particular of porosity, mechanical strength and abrasion resistance. However, the adsorption properties of these agglomerates are obviously reduced relative to the starting active powder due to the presence of agglomeration binder which is inert with respect to adsorption.

Various means have already been proposed for overcoming this drawback of the agglomeration binder being inert as regards the adsorption performance, among which is the transformation of all or at least part of the agglomeration binder into zeolite that is active from the adsorption viewpoint. This operation is now well known to those skilled in the art, for example under the name "zeolitization". To perform this operation readily, zeolitizable binders are used, usually belonging to the kaolinite family, and preferably precalcined at temperatures generally between 500° C. and 700° C.

Patent FR 2 925 366 describes a process for manufacturing LSX zeolite is agglomerates, with an Si/Al atomic ratio such that 1.00≤Si/Al≤1.15 exchanged with barium and optionally with barium and potassium, by agglomerating LSX zeolite crystals with a kaolin-based binder, followed by zeolitizing the binder by immersing the agglomerate in an alkaline liquor. After exchanging the cations of the zeolite with barium ions (and optionally potassium ions) and activation, the agglomerates thus obtained have, from the point of view of adsorption of the para-xylene contained in C8 aromatic fractions and of the mechanical strength, improved properties relative to adsorbents prepared from the same amount of LSX zeolite and binder, but whose binder is not zeolitized.

Besides high adsorption capacity and good selectivity properties in favour of the species to be separated from the reaction mixture, the adsorbent must have good mass transfer properties so as to ensure a sufficient number of theoretical plates to perform efficient separation of the species in admixture, as indicated by Ruthven in the book entitled *Principles of Adsorption and Adsorption Processes*, John Wiley & Sons, (1984), pages 326 and 407. Ruthven indicates (ibid., page 243) that, in the case of an agglomerated adsorbent, the global mass transfer depends on the sum of the intra-crystalline and inter-crystalline (between crystals) diffusional resistances.

The intra-crystalline diffusional resistance is proportional to the square of the diameters of the crystals and inverse or proportional to the intra-crystalline diffusivity of the molecules to be separated.

The inter-crystalline diffusional resistance (also known as the "macropore resistance") is itself proportional to the square of the diameters of the agglomerates, inversely proportional to the porosity contained in the macropores and mesopores (i.e. the pores with an aperture greater than 2 nm) in the agglomerate, and inversely proportional to the diffusivity of the molecules to be separated in this porosity.

The size of the agglomerates is an important parameter during the use of the adsorbent in industrial application, since it determines the loss of feedstock in the industrial unit and the filling uniformity. The particle size distribution of the agglomerates must thus be narrow, and centred on number-mean diameters typically between 0.40 mm and 0.65 mm so as to avoid excessive losses of feedstock.

The porosity contained in the macropores and mesopores in the agglomerate (the inter-crystalline macroporosity and mesoporosity, respectively) may be increased by using pore-forming agents, for instance corn starch as recommended in document U.S. Pat. No. 8,283,274 for improving the mass transfer. However, this porosity is does not participate in the adsorption capacity and the improvement of the macropore mass transfer then takes place to the detriment of the volume-based adsorption capacity. Consequently, this route for improving the macropore mass transfer proves to be very limited.

To estimate the improvement in transfer kinetics, it is possible to use the plate theory described by Ruthven in *Principles of Adsorption and Adsorption Processes*, ibid., pages 248-250. This approach is based on the representation of a column by a finite number of ideally stirred hypothetical reactors (theoretical stages). The equivalent height of theoretical plates is a direct measurement of the axial dispersion and of the resistance to mass transfer of the system.

For a given zeolite-based structure, a given size of adsorbent and a given operating temperature, the diffusivities are set, and one of the means for improving the mass transfer consists in reducing the diameter of the crystals. A gain in global mass transfer will thus be obtained by reducing the size of the crystals.

A person skilled in the art will thus seek to minimize the diameter of the zeolite crystals in order to improve the mass transfer.

Patent CN 1 267 185 C thus claims adsorbents containing 90% to 95% of zeolite BaX or BaXK for separating para-xylene, in which the zeolite X crystals are between 0.1 µm and 0.4 µm in size, so as to improve the mass transfer performance. Similarly, the application US 2009/0326308 describes a process for separating xylene isomers, the performance of which is improved by using adsorbents based on zeolite X crystals less than 0.5 µm in size. Patent FR 2 925 366 describes adsorbents containing LSX zeolite crystals with a number-mean diameter of between 0.1 µm and 4.0 µm.

The Applicant has nevertheless observed that the synthesis, filtration, handling and agglomeration of zeolite crystals whose size is less than 0.5 µm involve burdensome, uneconomical processes which are thus difficult to render industrializable.

Furthermore, such adsorbents comprising crystals less than 0.5 µm in size also prove to be more fragile, and it then becomes necessary to increase the content of agglomeration binder in order to reinforce the cohesion of the crystals with each other in the adsorbent. However, increasing the content of agglomeration binder leads to densification of the adsorbents, which causes an increase in the macropore diffusional resistance. Thus, despite a reduced intra-crystalline diffusional resistance due to the decrease in the size of the crystals, the increase in macropore diffusional resistance on account of the densification of the adsorbent does not allow an improvement in the overall transfer. Moreover, increasing the binder content does not make it possible to obtain a good adsorption capacity.

There is consequently still a need for improved zeolite-based adsorbent materials prepared from FAU zeolite crystals of LSX type that are easy to manipulate industrially, and for which said crystals (or constituent crystalline elements) are advantageously greater than 0.5 µm in size, and which have an improved global mass transfer relative to the adsorbents of identical crystal size known in the prior art, while at the same time conserving a high adsorption capacity and high adsorption selectivities for para-xylene with respect to its isomers.

These improved adsorbents would thus be particularly suitable for the gas-phase or liquid-phase separation of xylene isomers.

BRIEF SUMMARY OF THE INVENTION

A first object of the present invention is thus to propose zeolite-based adsorbents in the form of aggregates with optimized properties for the separation of gaseous or liquid mixtures of isomers and more particularly for the gas-phase or liquid-phase separation of xylenes, especially para-xylene of C8 aromatic fractions, and especially when said fractions are rich in ethylbenzene.

The zeolite-based adsorbents of the invention advantageously have selectivity properties for para-xylene with respect to its isomers of greater than 2.1, preferably greater than 2.3, and improved mass transfer properties, while at the same time having high mechanical strength and a high adsorption capacity, and are particularly suitable for use in a process for the liquid-phase separation of para-xylene, preferably of simulated counter-current type.

More precisely, the present invention relates to a zeolite-based adsorbent comprising at least one zeolite of FAU structure of LSX type and comprising barium and/or potassium, in which the outer surface area of said zeolite-based adsorbent, measured by nitrogen adsorption, is between 20 $m^2 \cdot g^{-1}$ and 100 $m^2 \cdot g^{-1}$, limits inclusive, and more preferentially between 20 $m^2 \cdot g^{-1}$ and 80 $m^2 \cdot g^{-1}$, limits inclusive, and even more preferentially between 30 $m^2 \cdot g^{-1}$ and 80 $m^2 \cdot g^{-1}$, limits inclusive.

Specifically, it has been observed by the Applicant that zeolite-based adsorbents with a controlled outer surface area, i.e. between 20 m²·g⁻¹ and 100 m²·g⁻¹, as measured by nitrogen adsorption, and prepared from LSX zeolite crystals with an Si/Al atomic ratio equal to 1.00±0.05 having a size of greater than 0.5 µm, have an improved global mass transfer when compared with zeolite-based adsorbents prepared from LSX zeolite crystals of identical Si/Al atomic ratio and size, but whose outer surface area, measured by nitrogen adsorption, is strictly less than 20 m²·g⁻¹

The present invention thus provides zeolite-based adsorbents with improved properties relative to the prior art, while at the same time facilitating the filtration, manipulation and agglomeration of the zeolite-based powders used during the manufacturing process. Another aim of the present invention consists in providing a process for preparing said adsorbents, and also the uses of said adsorbents for separating gaseous or liquid mixtures of isomers, more particularly of xylenes, and especially for separating very pure para-xylene from an aromatic hydrocarbon feedstock containing isomers containing 8 carbon atoms, and especially from a feedstock rich in ethylbenzene.

Yet another aim of the present invention consists in maximizing the mass transfer in the zeolite-based adsorbent, while at the same time maintaining high selectivities for para-xylene with respect to its isomers, especially greater than 2.1, and an adsorption capacity suitable for the application, at the same time as mechanical strength that is compatible with the application under consideration.

In the text hereinbelow, and unless otherwise indicated, the limits of a range of values are included in that range, especially in the expressions "between" and "from . . . to . . . ".

DETAILED DESCRIPTION OF THE INVENTION

Adsorbents According to the Invention

Figure 1:
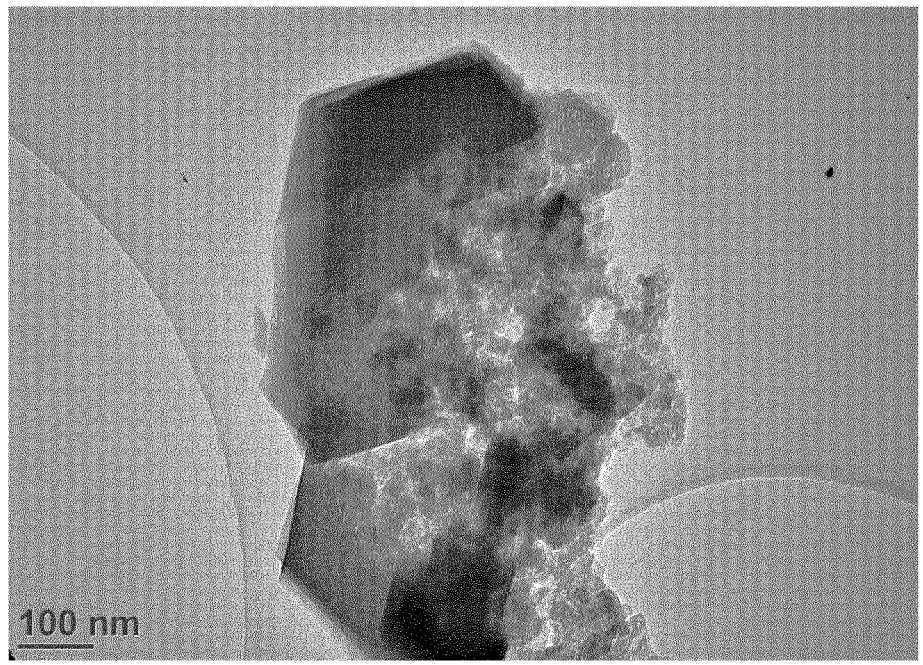
FIG. 1 shows a TEM of mesoporous crystals.

Thus, the present invention relates to a zeolite-based adsorbent:
 comprising at least one zeolite of FAU structure of LSX type
 comprising barium and/or potassium,
 for which the outer surface area, measured by nitrogen adsorption, is between 20 m²·g⁻¹ and 100 m²·g⁻¹, and preferentially between 20 m²·g⁻¹ and 80 m²·g⁻¹ and more preferentially between 30 and 80 m²·g⁻¹, limits inclusive.

In one embodiment, the zeolite-based adsorbent of the invention has an Si/Al atomic ratio of between 1.00 and 1.50, preferably between 1.00 and 1.40, limits inclusive, more preferably between 1.00 and 1.20, limits inclusive, and even more so preferably between 1.00 and 1.10, limits inclusive.

In a preferred embodiment of the invention, the zeolite of FAU structure of the zeolite-based adsorbent is a zeolite of FAU structure of LSX type (generally defined by its Si/Al atomic ratio=1.00±0.05), for which the number-mean diameter of the crystals is between 0.5 µm and 20 µm, limits inclusive, preferably between 0.5 µm and 10 µm, limits inclusive, more preferentially between 0.8 µm and 10 µm, limits inclusive, better still between 1 µm and 10 µm, limits inclusive, and more preferably between 1 µm and 8 µm, limits inclusive.

According to yet another preferred embodiment of the invention, the crystals have, in combination with the microporosity, internal cavities of nanometric size (mesoporosity), which are readily identifiable by observation using a transmission electron microscope (TEM) as described, for example, in U.S. Pat. No. 7,785,563.

The outer surface area of the zeolite-based adsorbent of the invention is calculated via the t-plot method from the nitrogen adsorption isotherm at a temperature of 77 K, after degassing under, vacuum (P<6.7×10⁻⁴ Pa), at a temperature of between 300° C. and 450° C. for a time ranging from 9 hours to 16 hours, preferably at 400° C. for 10 hours. The outer surface area of the FAU zeolite crystals of the adsorbent before agglomeration is measured in the same manner.

According to a preferred aspect, the barium (Ba) content of the zeolite-based adsorbent of the invention, expressed as barium oxide (BaO), is greater than 25%, preferably greater than 28%, very preferably greater than 34%, even more preferably greater than 37%, by weight relative to the total weight of the adsorbent, and, advantageously, the barium content, expressed as barium oxide (BaO), is between 28% and 42%, and typically between 37% and 40%, limits inclusive, by weight relative to the total weight of the adsorbent.

According to another preferred aspect, the potassium (K) content of the zeolite-based adsorbent of the invention, expressed as potassium oxide (K₂O), is less than 30%, preferably less than 15% and preferably between 0 and 10%, limits inclusive, by weight relative to the total weight of the adsorbent.

According to yet another preferred embodiment, the total content of alkali metal or alkaline-earth metal ions, other than barium and potassium, expressed as the total content of alkali metal or alkaline-earth metal ion oxides other than barium oxide BaO and potassium oxide K₂O, is between 0 and 5%, limits inclusive, relative to the total mass of the adsorbent.

Advantageously, the zeolite-based adsorbent according to the invention has a total volume contained in the macropores and mesopores (sum of the macropore volume and the mesopore volume) measured by mercury intrusion, of between 0.15 cm³·g⁻¹ and 0.5 cm³·g⁻¹, preferably between 0.20 cm³·g⁻¹ and 0.40 cm³·g⁻¹ and very preferably between 0.20 cm³·g⁻¹ and 0.35 cm³·g⁻¹, limits inclusive.

According to a preferred embodiment of the present invention, the zeolite-based adsorbent comprises macropores, mesopores and also micropores. The term "macropores" means pores whose diameter is greater than 50 nm. The term "mesopores" means pores whose diameter is between 2 nm and 50 nm, limits inclusive. The term "micropores" means pores whose diameter is less than 2 nm.

In addition, the adsorbent of the invention advantageously has a (macropore volume)/(macropore volume+mesopore volume) ratio of between 0.2 and 1 and very preferably between 0.5 and 0.9, limits inclusive.

In the context of the present invention, a zeolite-based adsorbent whose micropore volume, evaluated via the t-plot method from the nitrogen (N₂) adsorption isotherm at a temperature of 77 K, is greater than 0.160 cm³·g⁻¹, preferably between 0.170 cm³·g⁻¹ and 0.275 cm³·g⁻¹ and more preferably between 0.180 cm³·g⁻¹ and 0.250 cm³·g⁻¹, is also preferred. Said nitrogen adsorption isotherm is that also used for measuring the outer surface area via the t-plot method.

The crystalline structure of the FAU zeolite of LSX type in the zeolite-based adsorbent of the present invention is identifiable by x-ray diffraction (known to those skilled in the art by the abbreviation XRD).

According to another preferred embodiment, no zeolite-based structure other than the FAU structure is detected by x-ray diffraction in the zeolite-based adsorbent of the present invention.

The expression "no zeolite-based structure other than the FAU structure" means less than 5% and preferably less than 2% by weight, limits inclusive, of one or more zeolite-based phases other than the FAU structure. The mass fraction determined by XRD (technique described below) is expressed on a weight basis relative to the total weight of the adsorbent.

The zeolite-based adsorbent according to the invention also preferably comprises at least one non-zeolite-based phase which comprises, inter glia, an agglomeration binder used in the preparation method for ensuring the cohesion of the crystals with each other, whence the term "agglomerate" or "zeolite-based to agglomerate" occasionally used instead of the term "zeolite-based adsorbent" of the invention, as described previously.

In the present invention, the term "binder" means an agglomeration binder which ensures the cohesion of the zeolite crystals in the zeolite-based adsorbent (or agglomerated zeolite-based material) of the invention. This binder also differs from is the zeolite crystals in that it does not have a crystalline structure, and in particular does not have a zeolite-based crystalline structure, for which reason the binder is often termed inert, and more precisely inert with respect to adsorption and ion exchange.

According to a preferred embodiment, the mass fraction of FAU zeolite in the adsorbent is greater than or equal to 85% and preferably greater than or equal to 90% by weight, limits inclusive, relative to the total weight of the adsorbent of the present invention, the remainder to 100% preferably consisting of non-zeolite-based phase. According to a particularly advantageous aspect, the mass fraction of FAU zeolite is between 92% and 98% and preferably between 94% and 98% by weight, limits inclusive, relative to the total weight of the adsorbent of the present invention, the remainder to 100% preferably consisting of non-zeolite-based phase.

As already indicated, the mass fraction of zeolite(s) (degree of crystallinity) of the adsorbent according to the invention may be determined by x-ray diffraction analysis, known to those skilled in the art by the abbreviation XRD.

According to a preferred embodiment, the zeolite-based adsorbent according to the invention has a loss on ignition, measured at 950° C. according to standard NF EN 196-2, of between 3.0% and 7.7%, more preferably between 3.5% and 6.7% and advantageously between 4.0% and 6%, limits inclusive.

The zeolite-based adsorbent according to the present invention especially has, in combination, a mechanical strength, adsorption selectivities for para-xylene with respect to its isomers of greater than 2.1, preferably greater than 2.2, more preferably greater than 2.3, and an adsorption capacity that is also most particularly suitable for use in processes for the gas-phase or liquid-phase separation of xylene isomers.

In the context of the present invention, the mechanical strength is measured by the Shell method series SMS 1471-74 adapted for agglomerates less than 1.6 mm in size. This mechanical strength, measured for the zeolite-based adsorbent defined previously, is generally between 1.5 MPa and 4 MPa, preferably between 1.7 MPa and 4 MPa, more preferably between 1.8 MPa and 4 MPa and most preferably between 2 MPa and 4 MPa, limits inclusive.

Preparation of the Adsorbents According to the Invention

Another subject of the invention concerns a process for preparing the zeolite-based adsorbent as has just been defined, said process comprising at least the steps is of:

i) agglomeration of crystals of at least one zeolite of FAU structure of LSX type, having an outer surface area of between 20 $m^2 \cdot g^{-1}$ and 150 $m^2 \cdot g^{-1}$, limits inclusive, preferably between 20 $m^2 \cdot g^{-1}$ and 120 $m^2 \cdot g^{-1}$, more preferably between 20 $m^2 \cdot g^{-1}$ and 100 $m^2 \cdot g^{-1}$, limits inclusive, the number-mean diameter of the crystals of which is between 0.5 μm and 20 μm, limits inclusive, more preferably between 0.5 μm and 10 μm, limits inclusive, more preferentially between 0.8 μm and 10 μm, limits inclusive, better still between 1 μm and 10 μm, limits inclusive, and more preferably between 1 μm and 8 μm, limits inclusive, with a binder preferably comprising at least 80% of clay or of a mixture of clays and up to 5% of additives and also with the amount of water that allows the forming of the agglomerated material, followed by drying and calcination of the agglomerates;

b) optional step of zeolitization of all or part of the binder by placing the agglomerates obtained in step a) in contact with an aqueous basic solution;

c) cationic exchange(s) of the agglomerates of step b) by placing in contact with a solution of barium ions and/or of potassium ions;

d) optional additional cationic exchange of the agglomerates of step c) by placing in contact with a solution of potassium ions;

e) washing and drying of the agglomerates obtained in steps c) or d), at a temperature of between 50° C. and 150° C.; and f) production of the zeolite-based adsorbent according to the invention by activation of the agglomerates obtained in step e) under a stream of oxidizing and/or inert gas, especially with gases such as oxygen, nitrogen, air, a dry and/or decarbonated air, or an oxygen-depleted air, which is optionally dry and/or decarbonated, at a temperature of between 100° C. and 400° C., preferably between 200° C. and 300° C.

In a preferred embodiment of the process for preparing the zeolite-based adsorbent of the present invention, the drying of the agglomerates in step a) above is generally performed at a temperature of between 50° C. and 150° C., and the calcination of the dried agglomerates is generally performed under a stream of oxidizing and/or inert gas, especially with gases such as oxygen, nitrogen, air, a dry and/or decarbonated air, or an oxygen-depleted air, which is optionally dry and/or decarbonated, at a temperature above 150° C., typically between 180° C. and 800° C., preferentially between 200° C. and 650° C., for a few hours, for example from 2 hours to 6 hours.

In particular, said zeolite-based adsorbents are obtained from zeolite crystals with an outer surface area, measured by nitrogen adsorption, of between 20 $m^2 \cdot g^{-1}$ and 150 $m^2 \cdot g^{-1}$, and said zeolite crystals are preferably hierarchically porous zeolite crystals.

The term "hierarchically porous zeolite" means a zeolite bearing both micropores and mesopores, in other words a zeolite that is both microporous and mesoporous. The term "mesoporous zeolite" means a zeolite whose microporous zeolite crystals have, in combination with the microporosity, internal cavities of nanometric size (mesoporosity), which are readily identifiable by observation using a transmission electron microscope (TEM) as described, for example, in U.S. Pat. No. 7,785,563.

According to a preferred embodiment, the crystals of said zeolite of FAU structure of LSX type used in step a) have an Si/Al atomic ratio=1.00±0.05, measured by elemental chemical analysis, according to techniques that are well known to those skilled in the art and detailed hereinbelow.

It is possible to prepare said zeolite crystals with an outer surface area of between 20 $m^2 \cdot g^{-1}$ and 150 $m^2 \cdot g^{-1}$ by direct synthesis using structuring agents or by means of seeding techniques and/or by adjusting the synthetic operating conditions such as the $SiO_2/Al_2O_3$ ratio, the sodium content and the alkalinity of the synthetic mixture or by indirect synthesis according to conventional processes for post-treatment of FAU zeolite crystals known to those skilled in the art.

The post-treatment processes generally consist in removing atoms from the already-formed zeolite network, either by one or more acidic treatments which dealuminate the solid, these treatments being followed by one or more washes with sodium hydroxide (NaOH) so as to remove the aluminium-based residues formed, as described, for example, by D. Verboekend et al. (*Adv. Funct. Mater.*, 22, (2012), pp. 916-928), or alternatively by treatments which combine the action of an acid and that of a structuring agent which improve the efficacy of the acidic treatment, as described, for example, in application WO2013/106816.

The processes for the direct synthesis of these zeolites (i.e. synthetic processes other than the post-treatment) are preferred and generally involve one or more structuring agents or sacrificial templates.

The sacrificial templates that may be used may be of any type known to those skilled in the art and especially those described in application WO 2007/043731. According to a preferred embodiment, the sacrificial template is advantageously chosen from organosilanes and more preferentially from [3-(trimethoxysilyl)propyl]octadecyldimethylammonium chloride, [3-(trimethoxysilyl)propyl]hexadecyldimethylammonium chloride, [3-(trimethoxysilyl)propyl]dodecyldimethylammonium chloride, [3-(trimethoxysilyl) propyl]octylammonium chloride, N-[3-(trimethoxysilyl) propyl]aniline, 3-[2-(2-aminoethylamino)ethylamino] propyltrimethoxysilane, N-[3-(trimetho-xysilyl)propyl]-N'-(4-vinylbenzyl)ethylenediamine, triethoxy-3-(2-imidazolin-1-yl)propyl-silane, 1-[3-(trimethoxysilyl)propyl]urea, N-[3-(trimethoxysilyl)propyl]ethylenediamine, [3-(diethylamino) propyl]trimethoxysilane, (3-glycidyloxypropyl) trimethoxysilane, 3-(trimethoxysilyl)propyl methacrylate, [2-(cyclohexenyl)ethyl]triethoxysilane, dodecyltriethoxysilane, hexadecyltrimethoxysilane, (3-aminopropyl) trimethoxysilane, (3-mercaptopropyl)trimethoxysilane and (3-chloropropyl)trimethoxysilane, and also mixtures of two or more thereof in all proportions.

Among the sacrificial templates listed above, [3-(trimethoxysilyl)propyl]octadecyldimethylammonium chloride, or TPOAC, is most particularly preferred.

Use may also be made of sacrificial templates of higher molar mass, for example PPDA (Polymer Poly-DiallyldimethylAmmonium), PVB (PolyVinyl Butyral) and other oligomeric compounds known in the field for increasing the diameter of the mesopores.

According to a preferred embodiment of the process of the present invention, agglomeration of crystals of at least one hierarchically porous FAU zeolite of LSX type, as described previously, prepared in the presence of a sacrificial template intended to be removed, is performed in step a).

This removal may be performed according to the methods known to those skilled in the art, for example by calcination, and, in a non-limiting manner, the calcination of the zeolite crystals comprising the sacrificial template may be performed under a stream of an oxidizing and/or inert gas, especially with gases such as oxygen, nitrogen, air, a dry and/or decarbonated air, or an oxygen-depleted air, which is optionally dry and/or decarbonated, at one or more temperatures above 150° C., typically between 180° C. and 800° C., preferentially between 200° C. and 650° C., for a few hours, for example between 2 and 6 hours. The nature of the gases, the temperature increase ramps and the successive temperature stages and their durations will be adapted as a function of the nature of the sacrificial template.

The additional step of removal of the optional sacrificial template may be performed at any moment in the course of the process for preparing the zeolite-based adsorbent of the invention. The removal of said sacrificial template may thus advantageously be performed by calcination of the zeolite crystals before the agglomeration step a), or alternatively, concomitantly with the calcination of the adsorbent during step a).

However, it would not constitute a departure from the scope of the invention if the agglomeration of step a) comprised the agglomeration of several FAU zeolites of LSX type with an Si/Al atomic ratio equal to 1.00±0.05 and with an outer surface area measured by nitrogen adsorption of between 20 $m^2 \cdot g^{-1}$ and 150 $m^2 \cdot g^{-1}$ obtained according to different modes.

The synthesis of FAU zeolites of LSX type generally takes place in alkaline medium (sodium and potassium hydroxide and thus $Na^+$ and $K^+$ cations). The crystals of FAU zeolite of LSX type thus obtained predominantly, or even exclusively, comprise sodium and potassium cations. However, it would not constitute a departure from the scope of the invention to use crystals which have undergone one or more cationic exchanges, between the synthesis, before or after the optional removal of the sacrificial template if this step is carried out before performing step a). In this case, step c) and optionally the exchange step d) may optionally not be necessary.

The size of the crystals of FAU zeolite of LSX type used in step a) and of the crystals of FAU zeolite in the adsorbents according to the invention is measured by observation with a scanning electron microscope (SEM). As indicated previously, preferably, the number-mean diameter of the crystals is between 0.5 µm and 20 µm, limits inclusive, preferably between 0.5 µm and 10 µm, limits inclusive, more preferentially between 0.8 µm and 10 µm, limits inclusive, better still between 1 µm and 10 µm, limits inclusive, and more preferably between 1 µm and 8 µm, limits inclusive. In the present document, the term "number-mean diameter" or "size" is used especially for the zeolite crystals. The method for measuring these magnitudes is explained later in the description.

The agglomeration and forming of step a) may be performed according to any technique known to those skilled in the art, and in particular according to one or more of the techniques chosen from extrusion, compacting, agglomeration on a granulating plate, granulating drum, atomization and the like.

The proportions of agglomeration binder (see definition later) and of zeolite used are 8 parts to 15 parts by weight of binder for 92 parts to 85 parts by weight of zeolite.

After step a), the finest agglomerated adsorbents may be removed by cycloning and/or screening and/or the excessively coarse agglomerates may be removed by screening or crushing, in the case of extrudates, for example. The adsorbents thus obtained, whether in the form of beads, extrudates or the like, preferably have a volume-mean diameter, or their length (longest dimension when they are not spherical), of between 0.2 mm and 2 mm, in particular between 0.2 mm and 0.8 mm and preferably between 0.40 mm and 0.65 mm, limits inclusive.

The binder that may be used in the context of the present invention may be chosen from conventional binders known to those skilled in the art, which may or may not be zeolitizable, and preferably chosen from clays and mixtures of clays, silicas, aluminas, colloidal silicas, alumina gels, and the like, and mixtures thereof.

The clays are preferably chosen from kaolins, kaolinites, nacrites, dickites, halloysites, attapulgites, sepiolites, montmorillonites, bentonites, illites and metakaolins, and also mixtures of two or more thereof in all proportions.

During step a), besides the zeolite crystals, the binder may also comprise one or more additives. The additives are preferentially organic, for example lignin, starch, carboxymethylcellulose, surfactant molecules (cationic, anionic, nonionic or amphoteric), which are intended to facilitate the manipulation of the zeolite(s)/clay(s) paste by modification of the rheology and/or of the adhesive power or to give the final adsorbents satisfactory properties, especially in terms of macroporosity.

Mention may preferentially be made, but in a non-exhaustive manner, of methylcelluloses and derivatives thereof, lignosulfonates, polycarboxylic acids and carboxylic acid copolymers, amine derivatives thereof and salts thereof, especially alkaline salts and ammonium salts. The additives are introduced in a proportion of from 0 to 5% and preferably from 0.1% to 2% by weight relative to the total weight of the adsorbent.

The additives may also comprise a source of liquid and/or solid silica, preferably representing from 1% to 5% of the total mass of said solids. The optional source of silica may be of any type known to a person skilled in the art, who is a specialist in zeolite synthesis, for example colloidal silica, diatomaceous earth, perlite, fly ash, sand, or any other form of solid silica. For the calcination included in step a), the nature of the gases, the temperature increase ramps and the successive temperature stages, and also the respective durations thereof, will be adapted especially as a function of the nature of the sacrificial template to be removed and as is a function of the nature of the binder used in the agglomeration step a).

SEM observation of the zeolite-based adsorbent makes it possible to confirm the presence of a non-zeolite-based phase comprising, for example, agglomeration binder or any other amorphous phase in the adsorbents.

The cationic exchange steps c) and d) described above are performed according to the standard methods known to those skilled in the art, and usually by placing the adsorbents obtained from step a) or step b) in contact with a barium salt, such as barium chloride ($BaCl_2$) and/or a potassium salt (KCl) and/or a barium and potassium salt, in aqueous solution at a temperature between room temperature and 100° C., and preferably between 80° C. and 100° C. so as rapidly to obtain high barium contents, i.e. contents preferably greater than 25%, preferably greater than 28%, very preferably greater than 34% and even more preferably greater than 37%, expressed as weight of barium oxide relative to the total mass of the adsorbent.

Advantageously, the barium content expressed as barium oxide is between 28% and 42% and typically between 37% and 40%, limits inclusive, by weight relative to the total weight of the adsorbent. It is preferred to work with a large excess of barium ions relative to the cations of the zeolite that it is desired to exchange, typically an excess of the order of 10 to 12, advantageously by performing successive exchanges.

An optional potassium exchange in step d) may be performed before and/or after the barium exchange (step c). It is also possible in step a) to agglomerate crystals of zeolite of LSX type already containing barium or potassium ions or barium and potassium ions (pre-exchange of the cations present in the starting zeolite of LSX type, typically sodium and potassium cations, with barium or potassium ions or barium and potassium ions before step a) and to dispense with (or not) steps c) and/or d).

The Applicant has observed, surprisingly, that the cationic exchange step, which may be difficult on account of the relative fragility of the structure of the hierarchically porous zeolite crystals, does not affect the intrinsic properties of outer surface area and of micropore volume (related to the mass of the adsorbent once exchanged) of said hierarchically porous zeolite crystals.

After the cationic exchange step(s), washing is then performed, generally and preferably with water, followed by drying of the adsorbent thus obtained (step e). The activation that follows the drying (step f) is performed conventionally, according to the methods known to those skilled in the art, for example at a temperature is generally between 100° C. and 400° C., as indicated previously in step f) of the process.

The activation is performed for a time determined as a function of the desired loss on ignition. This time is generally between a few minutes and a few hours, typically between 1 hour and 6 hours.

Use of the Adsorbents According to the Invention

The present invention also relates to the uses of the zeolite-based adsorbents described above as adsorption agents advantageously capable of replacing the adsorption agents described in the literature, based on conventional crystals of FAU zeolite of LSX type, comprising barium and/or potassium, and especially in the uses listed below:
  separation of C8 aromatic isomer fractions and especially of xylenes,
  separation of substituted toluene isomers such as nitrotoluene, diethyltoluene, toluenediamine, and the like,
  separation of cresols,
  separation of polyhydric alcohols, such as sugars.

According to another subject, the present invention relates to a process for the gas-phase or liquid-phase separation of xylene isomers using at least one zeolite-based adsorbent as defined previously, and preferably in which the zeolite crystals of the zeolite-based adsorbent are prepared by direct synthesis using one or more structuring agents (or sacrificial templates).

In an alternative embodiment, the invention particularly relates to a process for separating para-xylene in a high purity (i.e. a purity greater than or equal to 90%) in a simulated bed from a feedstock of aromatic hydrocarbons containing isomers having 8 carbon atoms comprising the steps of:
  a. contacting the feedstock with a bed of adsorbents, comprising at least one zeolite-based adsorbent, as previously described, in order to preferentially adsorb para-xylene,
  b. contacting the adsorbent bed with a desorbent, said desorbent being preferably toluene or paradiethylbenzene, c. withdrawal from the adsorbent bed of a stream containing the desorbent and the less selectively adsorbed products of the feedstock,
d. withdrawal from the adsorbent bed of a stream containing the desorbent and the desired product, i.e. the para-xylene,
e. separation of the stream of step c) in a first stream containing the desorbent and a second stream containing the less selectively adsorbed products of the feedstock,
f. separation of the stream of step d) in a first stream containing the desorbent, and a second stream containing para-xylene in a purity being greater than or equal to 90%, preferably greater than or equal to 99%, and even more preferably greater than or equal to 99.7%.

The invention relates especially to a process for separating para-xylene from a feedstock of aromatic isomer fractions containing 8 carbon atoms, using as para-xylene adsorption agent a zeolite-based adsorbent as defined previously, and especially a FAU zeolite-based adsorbent of LSX type comprising barium and/or potassium and having a large outer surface area, characterized by nitrogen adsorption, typically between 20 $m^2 \cdot g^{-1}$ and 100 $m^2 \cdot g^{-1}$ and more preferentially between 20 $m^2 \cdot g^{-1}$ and 80 $m^2 \cdot g^{-1}$ and even more preferentially between 30 and 80 $m^2 \cdot g^{-1}$, limits inclusive, used in liquid-phase processes, but also in the gas-phase processes.

The separation process according to the invention may be performed by preparative adsorption liquid chromatography (in batch mode), and advantageously in continuous mode in a simulated moving bed unit, i.e. with simulated counter-current or simulated co-current, and more particularly with simulated counter-current.

The operating conditions of an industrial simulated moving bed adsorption unit, functioning in counter-current mode, are generally the following:
  number of beds: 4 to 24;
  number of zones: at least 4 operating zones, each being located between a feed point (stream of feedstock to be treated or stream of desorbent) and a withdrawal point (stream of raffinate or stream of extract);
  advantageously at a temperature of between 100° C. and 250° C., preferably between 140° C. and 190° C.;
  pressure between the bubble pressure of xylenes (or of toluene when toluene is chosen as desorbent) at the process temperature and 3 MPa;
  ratio of the flow rates of desorbent to feedstock: 0.7 to 2.5, preferably 0.7 to 2.0 (for example 0.9 to 1.8 for a stand-alone adsorption unit, and 0.7 to 1.4 for an adsorption unit combined with a crystallization unit);
  recycling rate: 2 to 12, preferably 2.5 to 6;
  cycle time, corresponding to the time between two injections of desorbent onto a given bed: advantageously between 4 and 25 minutes.

Reference may be made to the teaching of U.S. Pat. No. 2,985,589, U.S. Pat. No. 5,284,992 and U.S. Pat. No. 5,629,467.

The operating conditions of an industrial simulated co-current adsorption unit are generally the same as those operating in simulated counter-current mode with the exception of the recycling rate, which is generally between 0.8 and 7. Reference may be made to U.S. Pat. No. 4,402,832 and U.S. Pat. No. 4,498,991.

The desorbent is a desorption solvent whose boiling point is less than that of the feedstock, such as toluene, or higher than that of the feedstock, such as para-diethylbenzene (PDEB). Advantageously, the desorbent is toluene or para-diethylbenzene.

The selectivity of the adsorbents according to the invention for the adsorption of the para-xylene contained in C8 aromatic fractions is optimal when the loss on ignition thereof measured at 950° C. is preferably less than or equal to 7.7%, preferably between 0 and 7.7%, very preferably between 3.0% and 7.7%, more preferably between 3.5% and 6.5% and even more preferably between 4.5% and 6%, limits inclusive.

The water content in the inlet streams is preferentially adjusted to between 20 ppm and 150 ppm, for example by adding water to the feedstock and/or desorbent streams.

In addition, it has been noted that the selection of an outer surface area greater than 20 $m^2 \cdot g^{-1}$ as indicated previously makes it possible to reduce the transportation time to the micropores, leading to significantly improved mass transfer relative to the prior art.

Moreover, it has been noted that the selection of an outer surface area of between 20 $m^2 \cdot g^{-1}$ and 100 $m^2 \cdot g^{-1}$, as indicated previously, combined with the choice of a FAU zeolite of LSX type with an Si/Al atomic ratio equal to 1.00±0.05 makes it possible to obtain adsorption selectivities for para-xylene with respect to the other isomers that are sufficient for good separation, and especially selectivities for pare-xylene with respect to ethylbenzene, whose affinity for the adsorbent is the highest after para-xylene, of greater than 2.1.

It has been noted that the selectivity for para-xylene with respect to ethylbenzene of LSX-based adsorbents of the same Si/Al atomic ratio whose outer surface area is greater than 100 $m^2 \cdot g^{-1}$ or of adsorbents based on FAU zeolite of X type with an Si/Al atomic ratio of greater than 1.00±0.05 and with an outer surface area of between 20 $m^2 \cdot g^{-1}$ and 100 $m^2 \cdot g^{-1}$, is strictly less than 2.1.

Another advantage is that of being able to provide crystals of micrometric size (typically between 0.5 µm and 20 µm, limits inclusive, more preferably between 0.5 µm and 10 µm, limits inclusive, more preferentially between 0.8 µm and 10 µm, limits inclusive, better still between 1 µm and 10 µm, limits inclusive, and more preferably between 1 µm and 8 µm, limits inclusive) which are more easily manipulable, thus making the manufacture of adsorbents easier.

Thus, the zeolite-based adsorbents of the invention especially have improved mass transfer properties while at the same time maintaining optimum properties of selectivity for para-xylene with respect to its isomers, typically greater than 2.1, and also of adsorption capacity, and while conserving high mechanical strength for use in a process for the liquid-phase separation of para-xylene, preferably of simulated counter-current type.

Characterization Techniques
Particle Size of the Zeolite Crystals—Mesopore Detection Estimation of the number-mean diameter of the FAU zeolite crystals used during the agglomeration (step a) and of the crystals contained in the zeolite-based adsorbents according to the invention is performed by observation using a scanning electron microscope (SEM).

In order to estimate the size of the zeolite crystals on the samples, a set of images is taken at a magnification of at least 5000. The diameter of at least 200 crystals is then measured using dedicated software. The accuracy is of the order of 3%.

Figure 2:
FIG. 2 shows a TEM of filled crystals.

As indicated in U.S. Pat. No. 7,785,563, the transmission electron microscope (TEM) also makes it possible to check whether the zeolite crystals of the adsorbent of the present invention are filled zeolite crystals (i.e. non-mesoporous) or aggregates of filled zeolite crystals or mesoporous crystals (cf. the comparison of the TEM images of FIG. 1, in which the mesoporosity is clearly visible and FIG. 2 which shows filled crystals). TEM observation thus makes it possible to visualize the presence or absence of mesopores.

Chemical Analysis of the Zeolite-Based Adsorbents—Si/Al Ratio and Degree of Exchange:

An elemental chemical analysis of the final product obtained after steps a) to f) described previously may be performed according to various analytical techniques is known to those skilled in the art. Among these techniques, mention may be made of the technique of chemical analysis by x-ray fluorescence as described in standard NF EN ISO 12677:2011 on a wavelength-dispersive spectrometer (WDXRF), for example the Tiger S8 machine from the company Bruker.

X-ray fluorescence is a non-destructive spectral technique which exploits the photoluminescence of atoms in the x-ray range, to establish the elemental composition of a sample. Excitation of the atoms, generally with an x-ray beam or by electron bombardment, generates specific radiations after returning to the ground state of the atom. The x-ray fluorescence spectrum has the advantage of depending very little on the chemical combination of the element, which offers a precise determination, both quantitatively and qualitatively. A measurement uncertainty of less than 0.4% by weight is conventionally obtained after calibration for each oxide.

These elemental chemical analyses make it possible to check both the Si/Al atomic ratio of the zeolite used during the preparation of the adsorbent, and also the Si/Al atomic ratio of the adsorbent and to check the quality of the ionic exchange described in step c) and in the optional step d). In the description of the present invention, the measurement uncertainty of the Si/Al atomic ratio is ±5%.

The quality of the ionic exchange is linked to the number of moles of sodium oxide, $Na_2O$, remaining in the zeolite-based adsorbent after exchange. For example, the degree of exchange with barium ions is estimated by evaluating the ratio between the number of moles of barium oxide, $BaO$, and the number of moles of the combination ($BaO+Na_2O+K_2O$). Similarly, the degree of exchange with potassium ions is estimated by evaluating the ratio between the number of moles of potassium oxide, $K_2O$, and the number of moles of the combination ($BaO+K_2O+Na_2O$). It should be noted that the contents of the various oxides are given as weight percentages relative to the total weight of the anhydrous zeolite-based adsorbent.

Particle Size of the Zeolite-Based Adsorbents:

The determination of the volume-mean diameter of the zeolite-based adsorbents obtained after step a) of agglomeration and of forming is performed by analysis of the particle size distribution of a sample of adsorbent by imaging according to standard ISO 13322-2:2006, using a conveyor belt for passing the sample before the objective lens of the camera.

The volume-mean diameter is then calculated from the particle size distribution by applying standard ISO 9276-2: 2001. In the present document, the term "volume-mean diameter" or "size" is used for the zeolite-based adsorbents. The accuracy is of the order of 0.01 mm for the size range of adsorbents of the invention.

Mechanical Strength of the Zeolite-Based Adsorbents:

The crushing strength of a bed of zeolite-based adsorbents as described in the present invention is characterized according to the Shell method series SMS1471-74 (Shell Method Series SMS1471-74 *Determination of Bulk Crushing Strength of Catalysts. Compression-Sieve Method*), associated with the BCS Tester machine sold by the company Vinci Technologies. This method, initially intended for characterizing catalysts of 3 mm to 6 mm, is based on the use of a 425 μm screen, which will make it possible especially to separate the fines created during the crushing. The use of a 425 μm screen remains suitable for particles with a diameter of greater than 1.6 mm, but should be adapted according to the particle size of the adsorbents that it is desired to characterize.

The adsorbents of the present invention, generally in the form of beads or extrudates, generally have a volume-mean diameter or a length, i.e. longest dimension in the case of non-spherical adsorbents, of between 0.2 mm and 2 mm, in particular between 0.2 mm and 0.8 mm and preferably between 0.40 mm and 0.65 mm, limits inclusive. Consequently, a 100 μm screen is used instead of the 425 μm screen mentioned in the Shell method standard SMS1471-74.

Measuring protocol is as follows: a sample of 20 $cm^3$ of agglomerated adsorbents, prescreened with the appropriate screen (100 μm) and predried in an oven for at least 2 hours at 250° C. (instead of 300° C. mentioned in the Shell method standard SMS1471-74), is placed in a metal cylinder of known internal cross section. An increasing force is imposed in stages on this sample by means of a piston, through a bed of 5 $cm^3$ of steel beads so as better to spread the force exerted by the piston on the agglomerated adsorbents (use of beads 2 mm in diameter for particles of spherical shape with a diameter strictly less than 1.6 mm). The fines obtained at the various pressure stages are separated out by screening (suitable screen of 100 μm) and weighed.

The bulk crushing strength is determined by the pressure in megapascals (MPa) for which the amount of cumulative fines passing through the screen is 0.5% by weight of the sample. This value is obtained by plotting on a graph the mass of fines obtained as a function of the force applied to the bed of adsorbent and by interpolating to 0.5% by mass of cumulative fines. The mechanical bulk crushing strength is typically between a few hundred kPa and a few tens of MPa and generally between 0.3 MPa and 3.2 MPa. The accuracy is conventionally less than 0.1 MPa.

Identification and Quantification of the Zeolite Fractions of the Zeolite-Based Adsorbents and Estimation of the Lattice Parameter Identification of the zeolite fractions (by mass) contained in the adsorbent is performed by x-ray diffraction (XRD) analysis. This analysis is performed on a Brüker brand machine. Identification of the crystalline phases present in the zeolite-based adsorbent is performed by comparison with the ICDD database sheets and optionally by comparison with the diffractogram of a suitable reference (crystals of FAU zeolite of LSX type (assumed to be 100% crystalline) with an Si/Al atomic ratio equal to 1.00 and which have undergone the same cationic exchange treatments as the adsorbent under consideration). For example, the presence of type X zeolite exchanged with barium will be confirmed by comparison of the lines of the diffractogram obtained with ICDD sheet No. 38-0234 ("Zeolite X, (Ba)"). The comparison of the diffractograms is completed by a comparison of the lattice parameters measured on the reference zeolite and on the adsorbent under consideration. Measurement of the lattice parameter of the zeolite is performed with precision (to ±0.01 Å): to do this, an internal standard (Si 640b NIST certified) is added and the data are processed with the TOPAS refinement software. For example, a measurement taken on zeolite X crystals, with an Si/Al atomic ratio equal to 1.25, and 95% exchanged with barium, gives a lattice parameter of 25.02 Å±0.01 Å, whereas a measurement taken on LSX zeolite crystals, with an Si/Al atomic ratio equal to 1.00 and 95% exchanged with barium, gives a lattice parameter of 25.19 Å±0.01 Å.

The amount of the zeolite fractions (by mass) is evaluated from the relative intensities of the peaks in the diffractograms, taking as reference the peak intensities of the reference zeolite mentioned previously. The peaks, which make it possible to work back to the crystallinity, are the strongest peaks of the 2θangular zone between 9° and 37°, namely the peaks observed in the 2θangular ranges between 11° and 13°, between 22° and 26° and between 31° and 33°, respectively.

Micropore Volume and Outer Surface Area

The crystallinity of the zeolite-based adsorbents of the invention is also evaluated by measuring their micropore volume and by comparing this with that of a suitable reference (zeolite that is 100% crystalline under identical cationic treatment conditions or theoretical zeolite). This micropore volume is determined from the measurement of the adsorption isotherm of a gas, such as nitrogen, at its liquefaction temperature.

Prior to the adsorption, the zeolite-based adsorbent is degassed between 300° C. and 450° C. for a time of between 9 hours and 16 hours, under vacuum (P<$6.7 \times 10^{-4}$ Pa). Measurement of the nitrogen adsorption isotherm at 77 K is then performed on a machine of ASAP 2020 M type from Micromeritics, taking at least 35 measurement points at relative pressures of ratio $P/P_0$ between 0.002 and 1.

The micropore volume and the outer surface area are determined by the t-plot method from the isotherm obtained, by applying standard ISO 15901-3:2007 and by calculating the statistical thickness t via the Harkins-Jura equation. The micropore volume and the outer surface area are obtained by linear regression on the points of the t-plot between 0.45 nm and 0.57 nm, respectively from the y-axis to the origin and from the slope of the linear regression. The evaluated micropore value is expressed in $cm^3$ of liquid adsorbate per gram of anhydrous adsorbent. The outer surface area is expressed in $m^2$ per gram of anhydrous adsorbent.

Macropore and Mesopore Volume and Grain Density

The macropore and mesopore volumes and the grain density are measured by mercury intrusion porosimetry. An Autopore® 9500 mercury porosimeter from Micromeritics is used for analysing the distribution of the pore volume contained in the macropores and in the mesopores.

The experimental method, described in the machine's operating manual which makes reference to standard ASTM D 4284-83, consists in placing a sample of adsorbent (zeolite-based granular material to be measured) (of known loss on ignition) weighed beforehand, into a porosimetry cell and then, after first degassing (evacuation pressure of 30 μmHg for at least 10 minutes), in filling the cell with mercury to a given pressure (0.0036 MPa) and then in applying a pressure increasing in stages up to 400 MPa in order gradually to make the mercury penetrate into the pore network of the sample.

The relationship between the applied pressure and the apparent pore diameter is established by assuming cylindrical pores, a contact angle between the mercury and the wall of the pores of 140° and a mercury surface tension of 485 dynes/cm. The cumulative amount of mercury introduced as a function of the applied pressure is recorded. The value from which the mercury fills all the inter-granular voids is set at 0.2 MPa, and it is considered that beyond this value, the mercury penetrates into the pores of the granular material. The grain volume (Vg) is then calculated by subtracting the cumulative volume of mercury at this pressure (0.2 MPa) from the volume of the porosimetry cell, and by dividing this difference by the mass of the anhydrous equivalent granular material, i.e. the mass of said material corrected for the loss on ignition.

The grain density is the inverse of the grain volume (Vg), and is expressed in grams of anhydrous adsorbent per $cm^3$.

The macropore volume of the granular material is defined as being the cumulative volume of mercury introduced at a pressure of between 0.2 MPa and 30 MPa, corresponding to the volume contained in the pores with an apparent diameter of greater than 50 nm. The mesopore volume of the granular material is defined as being the cumulative volume of mercury introduced at a pressure of between 30 MPa and 400 MPa.

In the present document, the macropore and mesopore volumes of the zeolite-based adsorbents, expressed in $cm^3 \cdot g^{-1}$, are thus measured by mercury intrusion and relative to the mass of the sample as anhydrous equivalent, i.e. the mass of said material corrected for the loss on ignition.

Loss on Ignition of the Zeolite-Based Adsorbents:

The loss on ignition is determined under an oxidizing atmosphere, by calcination of the sample in air at a temperature of 950° C.±25° C., as described in standard NF EN 196-2 (April 2006). The measurement standard deviation is less than 0.1%.

Characterization of the Liquid-Phase Breakthrough Adsorption:

The technique used for characterizing the liquid-phase adsorption of molecules onto a porous solid is the technique known as breakthrough, described by Ruthven in *Principles of Adsorption and Adsorption Processes* (chapters 8 and 9, John Wiley & Sons, 1984), which defines the technique of breakthrough curves as the study of the response to the injection of a grade of adsorbable constituents. Analysis of the mean exit time (first moment) of the breakthrough curves gives information regarding the amounts adsorbed and also makes it possible to evaluate the selectivities, i.e. the separation factor, between two adsorbable constituents. The injection of a non-adsorbable constituent used as tracer is recommended for the estimation of the non-selective volumes. Analysis of the dispersion (second moment) of the breakthrough curves makes it possible to evaluate the equivalent height of to theoretical plates, based on the representation of a column by a finite number of ideally stirred hypothetical reactors (theoretical stages), which is a direct measurement of the axial dispersion and of the resistance to mass transfer of the system.

EXAMPLES

Example A: Synthesis of Conventional LSX Zeolite Crystals (Synthesis A of Patent FR 2 925 366) (Comparative Example)

Crystals are prepared according to synthesis A described in patent FR 2925366. The crystals obtained after filtration, washing and drying are identified by x-ray diffraction as faujasite. Chemical analysis of the solid gives an Si/Al ratio=1.01.

The micropore volume and the outer surface area measured according to the t-plot method from the nitrogen adsorption isotherm at 77 K after degassing under vacuum at 400° C. for 10 hours are, respectively, 0.305 $cm^3 \cdot g^{-1}$ and 6 $m^2 \cdot g^{-1}$.

Analysis of the size of the zeolite crystals is performed by scanning electron microscopy. The mean size of the crystals is 2.6 μm.

Example B: Synthesis of Hierarchically Porous FAU Zeolite Crystals

Example B1: Synthesis of HPX Type Zeolite Crystals with an Si/Al Ratio=1.24 and an Outer Surface Area Equal to 90 m²·g⁻¹ (Comparative Example)

A zeolite X with an outer surface area equal to 90 m²·g⁻¹ is synthesized directly according to the synthetic method described in the article by Inayat et al. (*Angew. Chem. Int. Ed.*, (2012), 51, 1962-1965).

Step 1): Preparation of the Growth Gel in the Reactor Stirred with Archimedean Screw at 300 Rpm A growth gel is prepared in a stainless-steel reactor equipped with a heating jacket, a temperature probe and a stirrer, by mixing an aluminate solution containing 119 g of sodium hydroxide (NaOH), 128 g of alumina trihydrate ($Al_2O_3$, $3H_2O$, containing 65.2% by weight of $Al_2O_3$) and 195.5 g of water at 25° C. over 25 minutes, with a stirring speed of 300 rpm, with a silicate solution containing 565.3 g of sodium silicate, 55.3 g of NaOH and 1997.5 g of water at 25° C.

The stoichiometry of the growth gel is as follows: 3.48 $Na_2O/Al_2O_3$/3.07 $SiO_2$/180 $H_2O$. Homogenization of the growth gel is performed with stirring at 300 rpm for 25 minutes at 25° C.

Step 2): Introduction of the Structuring Agent into the Reaction Medium 27.3 g of a solution of TPOAC at 60% in MeOH are introduced into the reaction medium with a stirring speed of 300 rpm (TPOAC/$Al_2O_3$ mole ratio=0.04). After 5 minutes of homogenization, the stirring speed is lowered to 50 rpm.

Step 3): Maturation Phase

The reaction medium is kept stirring at 50 rpm at 25° C. for 22 hours, and crystallization is then started.

Step 4): Crystallization

The stirring speed is maintained at 50 rpm, and the reactor jacket is set to a nominal value of 80° C. so that the reaction medium rises in temperature to 75° C. over 80 minutes. After 72 hours at a stage of 75° C., the reaction medium is cooled by circulating cold water through the jacket to stop the crystallization.

Step 5): Filtration/Washing

The solids are recovered on a sinter and then washed with the deionized water to neutral pH.

Step 6): Drying/Calcination

In order to characterize the product, drying is performed in an oven at 90° C. for 8 hours, and the loss on ignition of the dried product is 22% by weight.

Calcination of the dried product, which is necessary to release both the microporosity (water) and the mesoporosity by removing the structuring agent, is performed with the following temperature profile: 30 minutes of increase to 200° C., then 1 hour at a stage of 200° C., then 3 hours of increase to 550° C., and finally 1.5 hours at a stage of 550° C.

The micropore volume and the outer surface area measured according to the t-plot method from the nitrogen adsorption isotherm at 77 K after degassing under vacuum at 400° C. for 10 hours are, respectively, 0.260 cm³·g⁻¹ and 90 m²·g⁻¹. The number-mean diameter of the crystals of the mesoporous zeolite (or hierarchically porous zeolite) thus obtained is 4.5 μm and the Si/Al ratio is equal to 1.24.

In the text hereinbelow, a mass expressed as anhydrous equivalent means a mass of product minus its loss on ignition.

Example B2: Synthesis of HPLSX Type Zeolite Crystals with an Si/Al Ratio=1.01 and an Outer Surface Area Equal to 95 m²·g⁻¹ (According to the Invention)

Preparation of the Growth Gel: Reactor Stirred with Archimedean Screw at 250 Rpm A growth gel is prepared in a 3 liter stainless-steel reactor equipped with a heating jacket, a temperature probe and a stirrer, by mixing an aluminate solution containing 300 g of sodium hydroxide (NaOH), 264 g of 85% potassium hydroxide, 169 g of alumina trihydrate ($Al_2O_3$, $3H_2O$, containing 65.2% by weight of $Al_2O_3$) and 1200 g of water at 25° C. over 5 minutes, with a stirring speed of 250 rpm, with a silicate solution containing 490 g of sodium silicate, 29.4 g of NaOH and 470 g of water at 25° C.

The stoichiometry of the growth gel is as follows: 4.32 $Na_2O$/1.85 $K_2O/Al_2O_3$/2.0 $SiO_2$/114 $H_2O$. Homogenization of the growth gel is performed with stirring at 250 rpm for 15 minutes at 25° C.

b) Addition of the Nucleating Gel 11.6 g of nucleating gel (i.e. 0.4% by weight) of composition 12 $Na_2O/Al_2O_3$/10 $SiO_2$/180 $H_2O$ prepared in the same manner as the growth gel, and which has matured for 1 hour at 40° C., is added to the growth gel, at 25° C. with stirring at 300 rpm. After 5 minutes of homogenization at 250 rpm, the stirring speed is reduced to 50 rpm and stirring is continued for 30 minutes.

c) Introduction of the Structuring Agent into the Reaction Medium 35.7 g of a solution of TPOAC at 60% in methanol (MeOH) are introduced into the reaction medium with a stirring speed of 250 rpm over 5 minutes (TPOAC/$Al_2O_3$ mole ratio=0.04). A maturation step is then performed at 30° C. for 20 hours at 50 rpm before starting the crystallization.

d) 2-Step Crystallization

The stirring speed is maintained at 50 rpm and a linear increase in the nominal temperature of the reactor jacket to 63° C. is programmed so that the reaction medium increases in temperature to 60° C. over 5 hours followed by a stage of 21 hours at 60° C.; the nominal temperature of the reactor jacket is then set at 102° C. so that the reaction medium increases in temperature to 95° C. over 60 minutes. After 3 hours at a stage of 95° C., the reaction medium is cooled by circulating cold water through the jacket to stop the crystallization.

e) Filtration/Washing

The solids are recovered on a sinter and then washed with the deionized water to neutral pH.

f) Drying/Calcination

In order to characterize the product, drying is performed in an oven at 90° C. for 8 hours.

Calcination of the dried product, which is necessary to release both the microporosity (water) and the mesoporosity by removing the structuring agent, is performed by degassing under vacuum with a gradual increase in 50° C. steps up to 400° C. over a time of between 9 hours and 16 hours, under vacuum (P<6.7×10⁻⁴ Pa).

The micropore volume and the outer surface area measured according to the t-plot method from the nitrogen adsorption isotherm at 77 K after degassing under vacuum at 400° C. for 10 hours are, respectively, 0.215 cm$^3$·g$^{-1}$ and 95 m$^2$·g$^{-1}$. The number-mean diameter of the crystals is 6 μm. The mesopore diameters calculated from the nitrogen adsorption isotherm via the DFT method are between 5 nm and 10 nm. The x-ray diffractogram corresponds to a pure faujasite (FAU) structure, no LTA zeolite is detected. The Si/Al mole ratio of the HPLSX determined by x-ray fluorescence is equal to 1.01.

Example B3: Synthesis of HPLSX Zeolite Crystals with an Outer Surface Area Equal to 146 m$^2$·g$^{-1}$ (Comparative Example)

A hierarchically porous LSX zeolite of higher outer surface area than the zeolite synthesized in Example B2 is obtained by strictly following the procedure of Example B2, except for the TPOAC/Al$_2$O$_3$ mole ratio of step 2, which is equal to 0.07.

The micropore volume and the outer surface area measured according to the t-plot method from the nitrogen adsorption isotherm at 77 K after degassing under vacuum at 400° C. for 10 hours are, respectively, 0.198 cm$^3$·g$^{-1}$ and 146 m$^2$·g$^{-1}$. The number-mean diameter of the crystals of the mesoporous zeolite (or hierarchically porous zeolite) thus obtained is 6 μm and the Si/Al ratio is equal to 1.01.

Example 1: (Comparative)

Preparation of a Zeolite-Based Adsorbent in the Form of Granules with LSX Zeolite Crystals According to Example A, 2.6 μm in Diameter, and a Kaolin Type Binder.

An adsorbent is prepared by reproducing Example 6 described in patent FR 2 925 366, and grains are recovered, which are selected by screening in the particle size range between 0.3 mm and 0.5 mm, and such that the volume-mean diameter is 0.4 mm.

The degree of exchange with barium of this adsorbent, evaluated from the elemental chemical analysis by WDXRF, is 97% and its loss on ignition is 6.2%. The lattice parameter measured by XRD on this adsorbent is evaluated at 25.19 Å±0.01 Å. The micropore volume and the outer surface area measured according to the t-plot method from the nitrogen adsorption isotherm at 77 K after degassing under vacuum is at 400° C. for 10 hours are, respectively, 0.231 cm$^3$·g$^{-1}$ and 7 m$^2$ g$^{-1}$. The total volume contained in the macropores and the mesopores (sum of the macropore volume and of the mesopore volume), measured by mercury intrusion, is 0.25 cm$^3$·g$^{-1}$. The ratio (macropore volume)/(macropore volume+mesopore volume) is equal to 0.9. The mechanical strength of this adsorbent measured according to the method presented in the characterization techniques is 2.1 MPa.

Example 2: (Comparative)

Preparation of a Zeolite-Based Adsorbent in the Form of Granules with HPX Crystals 4.5 μm in Size and an Agglomeration Binder of Kaolin Type Such that the Outer Surface Area is Equal to 70 m$^2$·g$^{-1}$.

A homogeneous mixture consisting of 1600 g anhydrous equivalent of zeolite X crystals synthesized according to the procedure of Example B1 (crystal size 4.5 μm), 350 g anhydrous equivalent of kaolin, 130 g of colloidal silica sold under the trade name Klebosol® 30 (containing 30% by weight of SiO$_2$ and 0.5% of Na$_2$O), and also the amount of water which allows agglomeration of the mixture by extrusion, is prepared. The extrudates are dried, crushed so as to recover the grains in the particle size ranging between 0.3 mm and 0.5 mm, and such that the volume-mean diameter is 0.4 mm, and then calcined for 2 hours at 550° C. under a stream of nitrogen, and then for 2 hours at 550° C. under a stream of dry decarbonated air.

Barium exchange is then performed with a 0.7M concentration of barium chloride solution, BaCl$_2$, at 95° C. in 4 steps. At each step, the volume ratio of solution to mass of solid is 20 ml/g and the exchange is continued for 4 hours each time. Between each exchange, the solid is washed several times so as to free it of the excesses of salt. It is then dried at 80° C. for 2 hours and then activated at 250° C. for 2 hours under a stream of nitrogen.

The degree of barium exchange of this adsorbent, evaluated from the elemental chemical analysis by WDXRF, as described hereinabove in the analytical techniques, is 97% and the loss on ignition is 5.5%. The lattice parameter measured so by XRD on this adsorbent is evaluated at 25.02 Å±0.01 Å. The micropore volume and the outer surface area measured according to the t-plot method from the nitrogen adsorption isotherm at 77 K after degassing under vacuum at 400° C. for 10 hours are, respectively, 0.192 cm$^3$·g$^{-1}$ and 70 m$^2$·g$^{-1}$.

The total volume contained in the macropores and the mesopores (sum of the macropore volume and of the mesopore volume), measured by mercury intrusion, is 0.33 cm$^3$·g$^{-1}$. The ratio (macropore volume)/(macropore volume+mesopore volume) is equal to 0.6.

The mechanical strength of this adsorbent measured according to the method presented in the characterization techniques is 2.1 MPa, corresponding to the pressure required to obtain 0.5% of fines.

Example 3: (According to the Invention)

Preparation of a Zeolite-Based Adsorbent in the Form of Granules with HPLSX Crystals 6 μm in Size and an Agglomeration Binder of Kaolin Type such that the Outer Surface Area is Equal to 64 m$^2$·g$^{-1}$.

An adsorbent is prepared in an identical manner to the preparation of the adsorbent of Example 2, but using LSX zeolite crystals synthesized according to the procedure of Example B2 (crystal size 6 μm).

The degree of barium exchange of this adsorbent, evaluated from the elemental chemical analysis by WDXRF, as described hereinabove in the analytical techniques, is 97% and the loss on ignition is 5.0%. The lattice parameter measured by XRD on this adsorbent is evaluated at 25.20 Å±0.01 Å. The micropore volume and the outer surface area measured according to the t-plot method from the nitrogen adsorption isotherm at 77 K after degassing under vacuum at 400° C. for 10 hours are, respectively, 0.167 cm$^3$·g$^{-1}$ and 64 m2·g$_{-1}$.

The total volume contained in the macropores and the mesopores (sum of the macropore volume and of the mesopore volume), measured by mercury intrusion, is 0.29 cm$^3$·g$^{-1}$. The ratio (macropore volume)/(macropore volume+mesopore volume) is equal to 0.73.

The mechanical strength of this adsorbent measured according to the method presented in the characterization techniques is 2.3 MPa, corresponding to the pressure required to obtain 0.5% of fines.

Example 4: (Comparative)

Preparation of a Zeolite-Based Adsorbent in the Form of Granules with HPLSX Crystals 6 μm in Size and an Agglomeration Binder of Kaolin Type such that the Outer Surface Area is Equal to 121 m²·g⁻¹.

An adsorbent is prepared in an identical manner to the preparation of the adsorbent of Example 3, but using LSX zeolite crystals synthesized according to the is procedure of Example B3 (number-mean diameter of the crystals 6 μm).

The degree of barium exchange of this adsorbent, evaluated from the elemental chemical analysis by WDXRF, as described hereinabove in the analytical techniques, is 97% and the loss on ignition is 5.1%. The lattice parameter measured by XRD on this adsorbent is evaluated at 25.21 Å±0.01 Å. The micropore volume and the outer surface area measured according to the t-plot method from the nitrogen adsorption isotherm at 77 K after degassing under vacuum at 400° C. for 10 hours are, respectively, 0.147 cm³·g⁻¹ and 121 m²·g⁻¹.

The total volume contained in the macropores and the mesopores (sum of the macropore volume and of the mesopore volume), measured by mercury intrusion, is 0.34 cm³·g⁻¹. The ratio (macropore volume)/(macropore volume+mesopore volume) is equal to 0.63.

The mechanical strength of this adsorbent measured according to the method presented in the characterization techniques is 2.2 MPa, corresponding to the pressure required to obtain 0.5% of fines.

Example 5

A breakthrough test (frontal chromatography) is performed on the adsorbent of Example 2 and on the adsorbent of Example 3 according to the invention to evaluate their selectivity for the adsorption of para-xylene with respect to ethylbenzene. The amount of adsorbent used for this test is about 34 g.

The procedure for obtaining the breakthrough curves is as follows:
  filling of the column with the adsorbent and insertion in the test bench;
  filling with the desorption solvent at room temperature;
  gradual increase to 175° C. under a stream of solvent (5 cm³·min⁻¹);
  injection of solvent at 5 cm³·min⁻¹ when the adsorption temperature (175° C.) is reached;
  solvent/feedstock permutation to inject the feedstock (5 cm³·min⁻¹);
  collection and analysis of the breakthrough effluent; injection of the feedstock will be maintained until the concentration of solvent in the effluent is zero.

The desorption solvent used is para-diethylbenzene. The selectivity between two isomers is evaluated by using a feedstock containing 45% by weight of each of the isomers and 10% by weight of a tracer (isooctane) used for estimation of the non-selective volumes and not participating in the separation. The test performed uses a feedstock in which the feedstock composition is as follows:
  para-xylene: 45% by weight,
  ethylbenzene: 45% by weight,
  isooctane: 10% by weight The pressure is sufficient for the feedstock to remain in liquid phase at the adsorption temperature, i.e. 1 MPa. The surface speed is 0.2 cm·s⁻¹.

The selectivity for para-xylene relative to ethylbenzene is calculated from the amounts adsorbed of each compound, these amounts being determined by mass balance from the first moments of the breakthrough curves of all of the constituents Present in the effluent. The results are given in Table 1 below:

TABLE 1

| Example | Total xylene adsorption capacity (cm³·g⁻¹) | PX/EB selectivity |
|---|---|---|
| Adsorbent of Example 2 (comparative) | 0.178 | 2.06 |
| Adsorbent of Example 3 (invention) | 0.181 | 2.53 |
| Adsorbent of Example 4 (comparative) | 0.183 | 1.95 |

In the above table:
  the xylene adsorption capacity is expressed in cm³ of C8 aromatics adsorbed per gram of adsorbent;
  PX means para-xylene and EB means ethylbenzene The adsorbent products of Examples 2 to 4 have comparable total xylene adsorption capacities. On the other hand, the adsorbent of Example 3, according to the invention, has a selectivity between para-xylene and ethylbenzene of greater than 2.5, whereas the selectivity obtained with the adsorbents of Examples 2 and 4 is less than 2.1. The adsorbent of Example 3 will thus be more efficient for separating a feedstock rich in ethylbenzene.

Example 6

The purpose of Example 6 is to illustrate the gain in productivity obtained to with an adsorbent according to the invention (adsorbent of Example 3) relative to:
  an adsorbent with LSX zeolite crystals of non-conforming outer surface area (too low) according to the prior art (comparative adsorbent of Example 1),
  and an adsorbent of non-conforming outer surface area (too high) with LSX zeolite crystals of Si/Al ratio equal to 1.00±0.05 (adsorbent of Example 4).

The adsorbents of Examples 1, 3 and 4 are tested to evaluate their performance as regards the separation of para-xylene on a simulated counter-current pilot chromatography unit consisting of 15 columns in series 2 cm in diameter and 1.10 m in length. Circulation between the last and the first column takes place by means of a recycling pump. At each intercolumn connection, either a feedstock to be separated or desorbent may be injected. Either a raffinate or an extract may also be withdrawn. All the columns and the distribution valves are maintained at 175° C., and the pressure is maintained above 1.5 MPa. The shifts of the various injection or withdrawal points are simultaneous according to a permutation time that may be adjusted. The beds are divided into 4 chromatographic zones according to the following configuration:
  3 beds between the injection of desorbent and the withdrawal of extract defining zone 1
  6 beds between the withdrawal of extract and the injection of feedstock defining zone 2
  4 beds between the injection of feedstock and the withdrawal of raffinate defining zone 3
  2 beds between the withdrawal of raffinate and the injection of desorbent defining zone 4.

The feedstock is composed of 21.3% by mass of para-xylene, 19.6% of ortho-xylene, 45.1% of meta-xylene and 14.0% of ethylbenzene.

In a first stage, a test is performed using the adsorbent according to Example 1. This test makes it possible to determine the injection rates of feedstock and of desorbent required to obtain para-xylene in a purity of 99.7% and a yield of at least 97%.

para-Xylene is obtained in the extract in a purity of 99.7% and a yield of 97% by injecting the feedstock at a rate of 39.5 g·min$^{-1}$ and the desorbent at a rate of 35.5 g·min$^{-1}$ and by applying a permutation time of the injection and withdrawal points of 118 seconds. The flow rate of extract is 24.7 g·min$^{-1}$ and the flow rate of zone 4 is 105.9 g·min$^{-1}$.

Thereafter, all the adsorbents are tested by applying the same flow rate of desorbent. On the other hand, the feedstock flow rate, the permutation time of the injection and withdrawal points, and the recycling rate may be adjusted so as to achieve the required performance, namely a purity of 99.7% and a yield of 97%. The results are given in Table 2.

TABLE 2

| Adsorbent | Example 1 (comparative) | Example 3 (according to the invention) | Example 4 (comparative) |
|---|---|---|---|
| Outer surface area (m$^2$ · g$^{-1}$) | 7 | 64 | 121 |
| Column length (m) | 1.1 | 1.1 | 1.1 |
| Permutation time (s) | 118 | 66 | 65 |
| Desorbent flow rate (g · min$^{-1}$) | 35.5 | 35.5 | 35.5 |
| Extract flow rate (g · min$^{-1}$) | 24.7 | 19.9 | 19.5 |
| Zone 4 flow rate (g · min$^{-1}$) | 105.9 | 194.8 | 197.7 |
| Purity | 99.70% | 99.70% | 99.70% |
| Yield | 97.00% | 97.00% | 97.00% |
| Feedstock flow rate (g · min$^{-1}$) | 39.5 | 49.9 | 28.5 |

Figure 3:
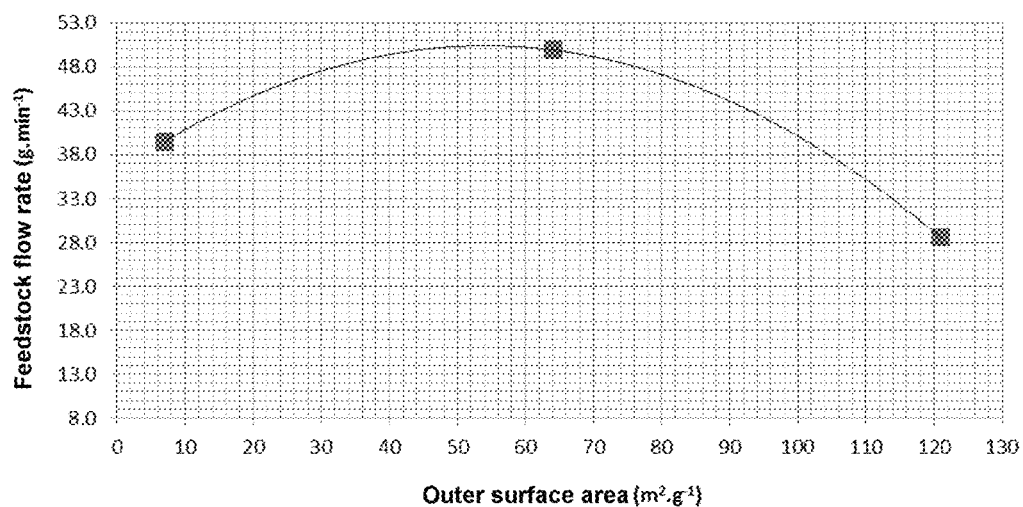
FIG. 3 illustrates the variation in the flow rate of feedstock as a function of the outer surface area.

FIG. 3 illustrates the variation in the flow rate of feedstock as a function of the outer surface area, the 3 points corresponding to Examples 1, 3 and 4 of Table 2.

Using adsorbent beads based on LSX crystals with an outer surface area of 64 m$^2$·g$^{-1}$, i.e. adsorbents according to the invention, it is possible to obtain a para-xylene with the required purity and yield performance, by injecting a feedstock flow rate greater than that treated with the reference adsorbent of Example 1, while at the same time injecting the reference desorbent flow rate, namely 35.5 g·min$^{-1}$, using identical columns.

For example, with the adsorbent of Example 3 according to the invention, para-xylene may be produced in a purity of 99.7% with a yield of 97% identical to those obtained with the reference adsorbent of Example 1, while at the same time increasing the feedstock flow rate by 26%. Consequently, for an identical specification, the productivity is increased by 26% with the adsorbent of Example 3 according to the invention relative to the adsorbent of Example 1.

Unlike the adsorbent products according to the invention, using adsorbent beads based on LSX crystals with an outer surface area greater than 100 m$^2$·g$^{-1}$, i.e. beyond the upper limit defined by the invention, it is not possible to obtain a para-xylene with the required purity and yield performance, by injecting a feedstock flow rate greater than or equal to that treated with the reference adsorbent of Example 1, while at the same time injecting the reference desorbent flow rate, namely 35.5 g·min$^{-1}$, using identical columns. On the contrary, to obtain the required purity and yield performance with adsorbents with an outer surface area greater than 100 m$^2$·g$^{-1}$, a feedstock flow rate lower than that treated with the reference adsorbent of Example 1 will be treated.

For example, with the adsorbent of Example 4 based on LSX crystals with an outer surface area equal to 121 m$^2$·g$^{-1}$, i.e. differing from the invention by an outer surface area greater than 100 m$^2$·g$^{-1}$, para-xylene may be produced in a purity of 99.7% with a yield of 97%, identical to those obtained with the reference adsorbent of Example 1, while at the same time reducing the feedstock flow rate by 28%. Consequently, for an identical specification, the productivity is reduced by 28% with the adsorbent of Example 4 relative to the adsorbent of Example 1.

Example 7

The purpose of Example 7 is to illustrate the gain in productivity obtained with an adsorbent according to the invention (adsorbent of Example 3) relative to an adsorbent having the same outer surface area, but with zeolite X crystals (adsorbent of Example 2), for feedstocks containing ethylbenzene.

The adsorbents of Examples 2 and 3 are tested to evaluate their performance as regards the separation of para-xylene on a simulated counter-current pilot chromatography unit consisting of 15 columns in series 2 cm in diameter and 1.10 m in length, operating identically to that described in Example 6.

Three feedstock compositions are used to evaluate the impact of the ethylbenzene content therein on the productivity of the adsorbents:

a feedstock composed of 21.3% by mass of para-xylene, 19.6% of ortho-xylene, 45.1% of meta-xylene and 14.0% of ethylbenzene by mass, as in the preceding example, a feedstock composed of 21.3% by mass of para-xylene, 23.8% of ortho-xylene and 54.9% of meta-xylene, this feedstock containing no ethylbenzene, a feedstock composed of 21.3% of para-xylene, 14.8% of ortho-xylene, 33.9% of meta-xylene and 30% of ethylbenzene by mass.

In Example 6, a test was performed using the adsorbent of Example 3 according to the invention. This test made it possible to determine the injection rates of feedstock and of desorbent required to obtain para-xylene in a purity of 99.7% and a yield of at least 97%, for the feedstock containing 14% of ethylbenzene.

para-Xylene is obtained in the extract in a purity of 99.7% and a yield of 97% by injecting the feedstock at a rate of 49.9 g·min$^{-1}$ and the desorbent at a rate of 35.5 g·min$^{-1}$ and by applying a permutation time of the injection and withdrawal points of 66 seconds. The flow rate of extract is 19.9 g·min$^{-1}$ and the flow rate of zone 4 is 194.8 g·m$^{-1}$.

Thereafter, the adsorbents of Example 2 and of Example 3 are tested with the various feedstocks by applying the same desorbent flow rate. On the other hand, the feedstock flow rate, the permutation time of the injection and withdrawal points, and the recycling rate may be adjusted so as to achieve the required performance, namely a purity of 99.7% and a yield of 97%. The results are given in Table 3 below:

TABLE 3

Change in the feedstock composition: % EB

| Adsorbent | Adsorbent based on X crystals Example 2 (comparative) | Adsorbent based on LSX crystals Example 3 (according to the invention) | Adsorbent based on X crystals Example 2 (comparative) | Adsorbent based on LSX crystals Example 3 (according to the invention) | Adsorbent Based on X crystals Example 2 (comparative) | Adsorbent based on LSX crystals Example 3 (according to the invention) |
|---|---|---|---|---|---|---|
| Outer surface area ($m^2 \cdot g^{-1}$) | 70 | 64 | 70 | 64 | 70 | 64 |
| Content of ethylbenzene in the feedstock (mass %) | 0% | 0% | 14% | 14% | 30% | 30% |
| Column length (m) | 1.1 | 1.1 | 1.1 | 1.1 | 1.1 | 1.1 |
| Permutation time (s) | 66 | 66 | 66 | 66 | 66 | 66 |
| Desorbent flow rate ($g \cdot min^{-1}$) | 35.5 | 35.5 | 35.5 | 35.5 | 35.5 | 35.5 |
| Extract flow rate ($g \cdot min^{-1}$) | 19.9 | 19.9 | 21.8 | 19.9 | 19.0 | 19.8 |
| Zone 4 flow rate ($g \cdot min^{-1}$) | 194.6 | 194.6 | 194.8 | 194.8 | 195.0 | 194.9 |
| Purity = | 99.70% | 99.70% | 99.70% | 99.70% | 99.70% | 99.70% |
| Yield = | 97.00% | 97.00% | 97.00% | 97.00% | 97.00% | 97.00% |
| Feedstock flow rate ($g \cdot min^{-1}$) | 50.7 | 50.7 | 47.8 | 49.9 | 44.6 | 48.7 |

Figure 4:
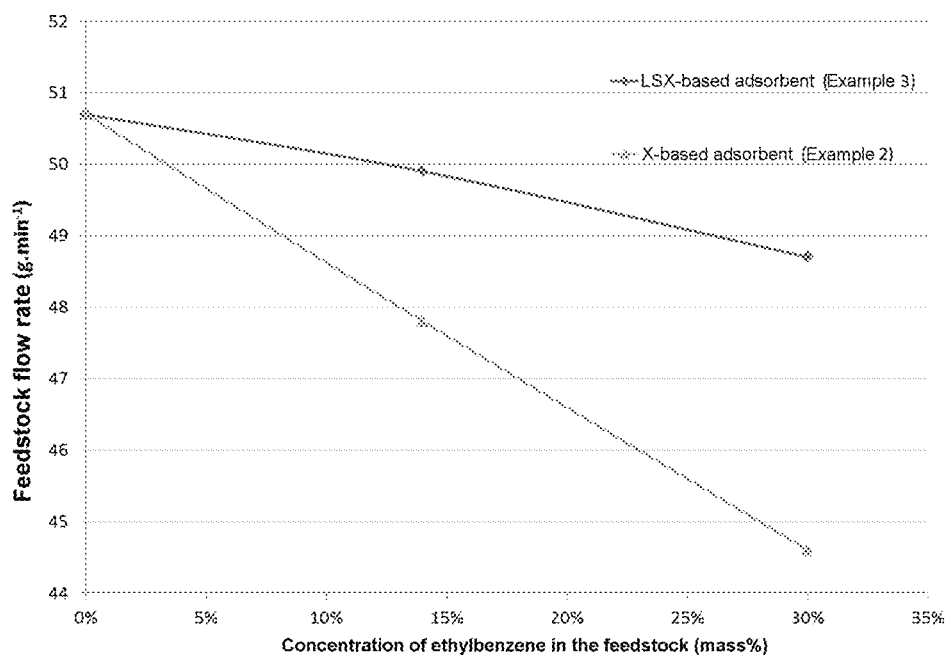
FIG. 4 illustrates the variation in the feedstock flow rate as a function of the content of ethylbenzene.

FIG. 4 illustrates the variation in the feedstock flow rate as a function of the content of ethylbenzene contained therein, in the case of the adsorbent according to Example 2 based on X crystals and in the case of the adsorbent according to Example 3 according to the invention based on LSX crystals.

In this example, using the adsorbent of Example 3 according to the invention, it is possible to obtain a para-xylene with the required purity and yield performance, by injecting a feedstock flow rate greater than or equal to that treated with the comparative adsorbent of Example 2, while at the same time injecting the reference desorbent flow rate, namely 35.5 g·min$^{-1}$, using identical columns, irrespective of the content of ethylbenzene obtained in the feedstock. It is also observed that the gain in productivity afforded by the adsorbent of Example 3 according to the invention is proportionately greater the higher the content of ethylbenzene. Less variability of productivity as a function of the content of ethylbenzene is also observed in the case of the adsorbent of Example 3 relative to the adsorbent of Example 2.

For a feedstock composition ranging between 0 and 30% of ethylbenzene, a variation in productivity of less than 5% is found in the case of the adsorbent of Example 3 according to the invention. In contrast, for the same variation in composition, a variation in productivity of greater than 12% is found in the case of the adsorbent of Example 2 according to the invention.

What is claimed is:

1. A zeolite-based adsorbent comprising at least one zeolite of FAU structure of LSX type, comprising at least one of barium or potassium, the zeolite-based adsorbent having an outer surface area, wherein the outer surface area of said zeolite-based adsorbent as measured by nitrogen adsorption is between 20 m$^2$·g$^{-1}$ and 100 m$^2$·g$^{-1}$, limits inclusive.

2. The zeolite-based adsorbent according to claim 1, wherein the zeolite of FAU structure is a zeolite of FAU structure of LSX type in the form of crystals having a number-mean diameter of between 0.5 μm and 20 μm, limits inclusive.

3. The zeolite-based adsorbent according to claim 1 having a content of barium (Ba) expressed as barium oxide (BaO) of greater than 25% by weight relative to the total weight of the adsorbent.

4. The zeolite-based adsorbent according to claim 1, having a content of potassium (K), expressed as potassium oxide (K$_2$O), of less than 30% by weight relative to the total weight of the adsorbent.

5. The zeolite-based adsorbent according to claim 1, wherein the zeolite-based adsorbent has macropores and mesopores, and wherein the total volume contained in the macropores and mesopores, measured by mercury intrusion, is between 0.15 cm$^3$·g$^{-1}$ and 0.5 cm$^3$·g$^{-1}$ limits inclusive.

6. The zeolite-based adsorbent according to claim 1 wherein the mass fraction of FAU zeolite in the adsorbant is greater than or equal to 85% by weight relative to the total weight of the adsorbent.

7. The zeolite-based adsorbent according to claim 1, wherein the zeolite-based adsorbent has a macropore volume and a mesopore volume and a ratio expressed as (macropore volume)/(macropore volume+mesopore volume) ratio of between 0.2 and 1, limits inclusive.

8. A process for preparing the zeolite-based adsorbent according to claim 1, said process comprising at least the steps of:
  a) agglomerating crystals of at least one zeolite of FAU structure of LSX type, the zeolite having an outer surface area of between 20 m$^2$·g$^{-1}$ and 150 m$^2$·g$^{-1}$, limits inclusive, the zeolite being in the form of crystals, wherein the number-mean diameter of the crystals is between 0.5 μm and 20 μm, limits inclusive, with a binder and also with an amount of water which allows forming of an agglomerated material, followed by drying and calcination of the agglomerated material;
  b) optionally, carrying out a step involving zeolitization of all or part of the binder by placing the agglomerated material obtained in step a) in contact with an aqueous basic solution;
  c) carrying out cationic exchange(s) of the agglomerated material of step b) by placing the agglomerated material in contact with a solution of at least one of barium ions or potassium ions;
  d) optionally, carrying out additional cationic exchange of the agglomerated material of step c) by placing the agglomerated material in contact with a solution of potassium ions;

e) washing and drying of the agglomerates obtained in steps c) or d), at a temperature of between 50° C. and 150° C.; and f) producing the zeolite-based adsorbent by activation of the agglomerates obtained in step e) under a stream of a gas selected from the group consisting of oxidizing gases and inert gases, wherein the gas is at a temperature of between 100° C. and 400° C.

9. A process according to claim 8, wherein the binder is comprised of at least one clay selected from the group consisting of kaolins, kaolinites, nacrites, dickites, halloysites, attapulgites, sepiolites, montmorillonites, bentonites, illites and metakaolins, and mixtures thereof in all proportions.

10. A process, comprising using a zeolite-based adsorbent according to claim 1 as an adsorption agent in:
   separating C8 aromatic isomer fractions,
   separating substituted toluene isomers,
   separating cresols, or
   separating polyhydric alcohols.

11. A separation process for gas-phase or liquid-phase separation of xylene isomers using at least one zeolite-based adsorbent according to claim 1.

12. The separation process according to claim 11, wherein the process is a process for separating para-xylene from a feedstock of aromatic isomer fractions containing 8 carbon atoms.

13. The process according to claim 12, wherein the process is performed in a simulated moving bed industrial adsorption unit, functioning in counter-current mode, under the following operating conditions:
   number of beds: 4 to 24;
   number of zones: at least 4 operating zones, each being located between a feed point and a withdrawal point;
   temperature between 100° C. and 250° C.;
   pressure between the bubble pressure of xylenes (or of toluene when toluene is chosen as desorbent) at the process temperature and 3 MPa;
   ratio of the flow rates of desorbent to feedstock to be treated: 0.7 to 2.5;
   recycling rate: 2 to 12, preferably 2.5 to 6;
   cycle time, corresponding to the time between two injections of desorbent onto a given bed: between 4 and 25 minutes.

14. The process according to claim 13, wherein the desorbent is toluene or para-diethylbenzene.

15. The process according to claim 13 wherein the inlet streams have a water content which is adjusted to between 20 ppm and 150 ppm.

16. The zeolite-based adsorbent comprising of claim 1 wherein the outer surface area of said zeolite-based adsorbent, as measured by nitrogen adsorption, is between 30 and 80 $m^2 \cdot g^{-1}$, limits inclusive.

17. The zeolite-based adsorbent according to claim 2, wherein the zeolite of FAU structure is a zeolite of FAU structure of LSX type for which the number-mean diameter of the crystals is between 1 μm and 8 μm, limits inclusive.

18. The zeolite-based adsorbent according to claim 3, wherein the content of barium (Ba) expressed as barium oxide (BaO) is greater than 37% by weight relative to the total weight of the adsorbent.

19. The zeolite-based adsorbent according to claim 4, wherein the content of potassium (K), expressed as potassium oxide ($K_2O$), is between 0 and 10%, limits inclusive, by weight relative to the total weight of the adsorbent.

20. The zeolite-based adsorbent according to claim 5, wherein the total volume contained in the macropores and mesopores, measured by mercury intrusion, is between 0.20 $cm^3 \cdot g^{-1}$ and 0.35 $cm^3 \cdot g^{-1}$, limits inclusive.

21. The zeolite-based adsorbent according to claim 6, wherein the mass fraction of FAU zeolite in the adsorbent is greater than or equal to 90% by weight relative to the total weight of the adsorbent.

22. The zeolite-based adsorbent according to claim 7, wherein the ratio expressed as (macropore volume)/(macropore volume+mesopore volume) ratio is between 0.5 and 0.9, limits inclusive.

* * * * *